United States Patent
Balachandran et al.

(10) Patent No.: US 10,820,978 B2
(45) Date of Patent: Nov. 3, 2020

(54) IMPLANTS AND METHODS FOR TREATMENTS OF PELVIC CONDITIONS

(71) Applicant: Boston Scientific Scimed, Inc., Maple Grove, MN (US)

(72) Inventors: Ram Kumar Balachandran, Maple Grove, MN (US); Thomas A. Albrecht, Edina, MN (US); John A. Bostrom, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 834 days.

(21) Appl. No.: 15/489,211

(22) Filed: Apr. 17, 2017

(65) Prior Publication Data
US 2017/0304037 A1    Oct. 26, 2017

Related U.S. Application Data

(60) Provisional application No. 62/325,269, filed on Apr. 20, 2016.

(51) Int. Cl.
*A61F 2/00*    (2006.01)

(52) U.S. Cl.
CPC .... *A61F 2/0045* (2013.01); *A61F 2220/0025* (2013.01); *A61F 2230/006* (2013.01); *A61F 2250/0008* (2013.01); *A61F 2250/0018* (2013.01)

(58) Field of Classification Search
CPC .... A61F 2/0004; A61F 2/0031; A61F 2/0036; A61F 2/0045; A61F 2/0063; A61F 2/0077; A61F 2220/0025
See application file for complete search history.

(56) References Cited

U.S. PATENT DOCUMENTS

| | | |
|---|---|---|
| 8,109,867 B2 | 2/2012 | Rosenblatt |
| 8,720,446 B2 | 5/2014 | Deitch |
| 8,956,276 B2 | 2/2015 | Young et al. |
| 9,060,836 B2 | 6/2015 | Jagger et al. |
| 2002/0028980 A1 | 3/2002 | Thierfelder et al. |
| 2008/0021265 A1* | 1/2008 | Garbin ............ A61B 17/06109 600/30 |
| 2010/0184805 A1 | 7/2010 | Baldwin et al. |
| 2012/0184805 A1 | 7/2012 | Pulliam et al. |
| 2013/0109910 A1 | 5/2013 | Alexander et al. |
| 2014/0005471 A1 | 1/2014 | Amarasinghe et al. |
| 2014/0257032 A1 | 9/2014 | Hacker et al. |
| 2015/0057491 A1 | 2/2015 | Goddard et al. |

FOREIGN PATENT DOCUMENTS

| | | |
|---|---|---|
| EP | 1608271 A1 | 12/2005 |
| JP | 2013516244 A | 5/2013 |
| WO | 2007/149348 A2 | 12/2007 |
| WO | 2011/106419 A1 | 9/2011 |

OTHER PUBLICATIONS

International Search Report and Written Opinion for PCT Patent Application No. PCT/US2017/028087, dated Oct. 20, 2017, 13 pages.

* cited by examiner

*Primary Examiner* — Carrie R Dorna
(74) *Attorney, Agent, or Firm* — Brake Hughes Bellermann LLP

(57) ABSTRACT

The present invention relates to surgical implants with adjustable size features, and methods for treating pelvic conditions by use of the implants.

20 Claims, 10 Drawing Sheets

IMPLANTS AND METHODS FOR TREATMENTS OF PELVIC CONDITIONS

CROSS-REFERENCE TO RELATED APPLICATION

This application is a Nonprovisional of, and claims priority to, U.S. Patent Application No. 62/325,269, filed on Apr. 20, 2016, entitled "Implants and Methods for Treatments of Pelvic Conditions", which is incorporated by reference herein in its entirety.

FIELD OF THE INVENTION

The present invention relates to surgical implants that include implant material, and reinforcement that is effective to adjust a mechanical property of the implant material, the surgical implant being useful for any of a variety of different surgical procedures, such as for treating a pelvic condition (e.g., incontinence, prolapse, levator avulsion), a heart condition, a hernia, etc.

BACKGROUND

Surgical implants are used in a large variety of different surgical treatments. Some forms of implants are constructed of materials that include a generally planar, flexible, fabric-type implant material. These implants can be used for treating conditions of soft tissue, such as in treating cardiac tissue, hernias, pelvic conditions such as incontinence and prolapse, as well as for treating other medical conditions by a method that uses the implant material to support soft tissue.

Regarding pelvic health, this is a medical area of increasing importance for both men and women, due at least in part to an aging population. Examples of common pelvic ailments include incontinence (e.g., urinary or fecal), pelvic tissue prolapse (e.g., female vaginal prolapse or levator prolapse), prolapse of the uterus or bladder, and conditions of the pelvic floor muscles such as levator avulsion. Specific vaginal prolapse conditions include non-apical conditions such as cystocele and rectocele, as well as vaginal vault prolapse (i.e., apical prolapse). Pelvic disorders such as these can result from weakness or damage to normal pelvic support systems.

A form of non-apical prolapse is prolapse of tissue of an anterior vaginal wall, e.g., cystocele. Rectocele, in contrast, is a form of non-apical posterior vaginal prolapse, i.e., prolapse of posterior vaginal wall tissue. An enterocele is a vaginal hernia in which the peritoneal sac containing a portion of the small bowel extends into the rectovaginal space. Apical prolapse, also referred to as vaginal vault prolapse, is a distension of (i.e., Application Publications 2002/0028980; 2010/0184805; 2014/0005471; 2015/0057491; and U.S. Pat. Nos. 8,109,867; 8,720,446; and 8,956,276.

Sacrocolpopexy procedures are known, and involve surgically removing the uterus of the patient (hysterectomy), if the uterus is present, followed by the suspension of the vaginal walls or apex from the sacrum using a synthetic mesh. This procedure places the vaginal apex back in its anatomical position, and retains the tissue in place by means of the implanted mesh. The procedure allows restoration of vaginal length and axis without compromising its caliber and is therefore likely to have a favorable functional outcome.

According to certain SCP procedures, the surgical implant is a mesh that is preformed into the shape of a "Y," having two anterior leafs connected to a single posterior or distal leaf. In use, the two anterior "leafs" (or "arms" or "appendages") of the "Y"-shaped implant are surgically secured to the anterior vaginal wall and the posterior vaginal wall of a patient. The third portion of the Y-shaped mesh (i.e., the sacral leaf or sacral tail) is secured in a posterior direction at or near a sacrum, such as at a patient's anterior longitudinal ligament. Examples of Y-shaped surgical implants that are currently sold commercially either have the two vaginal appendages knit together seamlessly to form the sacral tail (BARD Alyte implant, ASTORA Y-mesh implant), or have the vaginal appendages and the sacral tail securely joined together at a three-way junction with the sacral leaf (Coloplast Restorelle implant, Boston Scientific Upsylon implant, Caldera Vertessa implant).

A sacrocolpopexy procedure for treating apical prolapse, as typically performed using a commercially available preformed non-adjustable Y-type implant, includes initial steps of suturing the two vaginal portions (leafs, appendages) of the implant to the anterior and posterior vaginal walls, adjacent to the vaginal apex. After attachment of the vaginal leafs to the vaginal tissues, a desired tension, i.e., an amount of tension required to suspend the vaginal tissue from the sacrum, is identified, and the sacral tail of the implant is surgically attached at or near the sacrum. Determining the right amount of tension to place on the implant through the sacral leaf is critical to the success of the procedure. Too much tension can result in complications like urinary incontinence. Too little tension can cause recurring prolapse.

Previously, adjustable implants have also been described as useful for treating apical vaginal prolapse. See, e.g., US patent publication 2012/0184805. But it is not believed that previous implants have been used with methods of treating non-apical prolapse by sequences of method steps as described herein, or to place differential tension and support to non-apical posterior and anterior vaginal tissue, e.g., using a non-transvaginal method.

SUMMARY

According to the invention, an adjustable Y-type surgical implant useful for treating vaginal prolapse, e.g., apical prolapse, non-apical vaginal prolapse, or both, can be used to provide improved positioning and therapeutic effect of anterior and posterior vaginal leafs of the implant, by providing differential tension and support at the posterior and vaginal tissues, when the implant surgically placed.

Y-shaped, pre-formed and non-adjustable surgical implants useful for SCP procedures have a fixed overall length, fixed sizes (including lengths) of the two vaginal leafs extending from the sacral leaf, and a fixed size (including length) of the sacral leaf. This type of implant, being non-adjustable as to its size features, is typically placed in a manner that distributes the tension placed at the sacral tail equally between the anterior and the posterior vaginal appendages (leafs) of the mesh. See FIG. 2, wherein T1 is approximately equal to T2. This type of equal distribution of tension and support between the two vaginal leafs is desirable and useful in patients who primarily have vaginal vault (i.e., apical) prolapse.

In patients who have varying levels of cystocele or rectocele, or both, i.e., non-apical prolapse, optionally in combination with apical prolapse, a surgical treatment of the condition may be improved by placing a different amount of tension on the anterior vaginal wall relative to the tension placed on the posterior vaginal wall. For example, if the patient has significant anterior wall prolapse when compared to the posterior wall, the anterior vaginal wall would benefit from an additional amount of support compared to the posterior wall. 1bis would require that more tension be placed on the anterior appendage (i.e., the anterior vaginal leaf) of the Y-shaped implant attached to the anterior vaginal tissue, compared to the amount of tension placed on the posterior appendage attached to the posterior vaginal tissue. If a standard Y-shaped implant is used in such cases with the sacral tail tension determined based on the appropriate amount of anterior wall support, then it could result in excess tension on the posterior side leading to complications (see FIG. 2). This is because the way by which surgeons typically tension a pre-formed Y-mesh is exclusively by the amount of tension placed on the sacral tail.

According to the present invention, a physician may desire to differentially tension the anterior and the posterior appendages of the Y-type {Y-shaped) implant during surgical placement of the implant, to cater to the wide variety of prolapse conditions that the surgeon deals with on a regular basis. Non-adjustable Y-type implants do not provide the surgeon with a capability to place different levels of tension on anterior versus posterior vaginal tissue by adjusting the implant, and are normally placed in a manner that equally distributes the tension of the sacral tail (sacral leaf) between the two vaginal appendages (between the anterior vaginal leaf and the posterior vaginal leaf).

As one way to avoid the limitations of pre-formed non-adjustable Y-type implants, physicians may at present currently use two separate mesh implant pieces: one piece for the anterior vaginal wall and a second piece for the posterior wall, attaching both pieces separately to the sacrum. See FIG. 1. With two mesh pieces, the surgeon can control the amount of tension on each one separately and achieve a desired outcome of differential tensioning at the anterior and posterior vaginal tissue. The downside to this solution is that the two individual pieces of mesh must be surgically attached (e.g., sutured) separately to the sacrum. Attaching the two ends of the two mesh pieces separately to the sacrum is one of the riskiest steps of the procedure, given the proximity of the attachment points to major blood vessels and the ureter. So the probability of causing significant harm to the patient increases two-fold when the suturing is done twice, due to the need to separately attach two pieces of mesh. This solution also increases the total procedure time as sacral attachment is typically a time consuming step and must be done twice.

According to the invention, new methods are described for treating vaginal prolapse wherein an adjustable implant is used to selectively distribute tension placed on an anterior portion, and, independently on a posterior portion of vaginal tissue. Depending on a particular prolapse condition of a patient, support provided to posterior vaginal tissue can be applied at a different level as compared to support provided at anterior vaginal tissue. For example, an amount of anterior tension relative to posterior tension can be selected based on the specific variety and combination of prolapsed tissue present at the vaginal tissue of the patient, particularly the presence and the relative degree of prolapse found at non-apical anterior vaginal tissue compared to the degree of prolapse found at non-apical posterior tissue of the patient. According to certain methods, vaginal leafs of an adjustable implant can be attached to anterior and posterior vaginal tissue, e.g., non-apical tissue at an anterior vaginal wall and a posterior vaginal wall. After the vaginal leafs are secured to the vaginal tissues, the length or lengths of one or two vaginal leafs can be adjusted. Adjusting the length or lengths of the vaginal leafs can produce differential tension and differential support applied to the different vaginal tissues supported by each of the two vaginal leafs. Subsequently, the amount of tension desired to be present in the sacral leaf can be determined, and the sacral leaf can be attached to tissue at a region of sacral anatomy.

Implants useful in the present description can be any Y-type implant that includes adjustability features that allow differential support of non-apical anterior vaginal tissue relative to non-apical posterior vaginal tissue. Non-limiting examples of useful implants are described herein, including those described as having a moveable connector attached to a fixed-length base.

As used herein, the term "distal," with reference to a patient's anatomy or a device, a portion of a device, or a method described herein, refers to a direction toward a posterior of the patient, e.g., toward a sacrum relative to a vagina or uterus, and the term "proximal," with reference to a patient's anatomy or a device or method described herein, refers to a direction toward an anterior of the patient, e.g., in a direction toward vaginal tissue or a urethra relative to a sacrum.

The term "securely attached" as used herein refers to an attachment between two structures, e.g., between an implant material of a leaf or base of an implant, and a connector of the implant, in a manner by which the two structures will not become separated during normal use and operation of a device as described, including for example surgical placement of the leafs and movement of a moveable connector; the two structures can be separated only by application of a substantial force that would result in tearing, ripping, or cutting of at least one of the structures in a manner that would substantially damage the device. As an example, the two structures can be attached in a manner that will cause them to necessarily remain attached for the purposes of surgical placement and use of the implant. The "securely attached" structures may be held together by any useful securing mechanism or technique, such as by adhesive, by thermoplastic bonding (e.g., molding), by ultrasonic bonding, by a permanent or secure frictional engagement such as a clasp or a jagged surface, or by another attachment mechanism that is designed and able to hold the two structures together during and after surgical placement of the implant.

The term "moveably attached," as in a moveable connector that is moveably attached to a base along a width of the base, refers to an engagement between these two structures that allows the connector to maintain engagement with the base while moving along the length of the base. The moveable connector is attached to the base and is in contact with the base in a manner that allows the slider to move (e.g., slide) to different locations along the length of the based while maintaining contact with the base.

Figure 1:
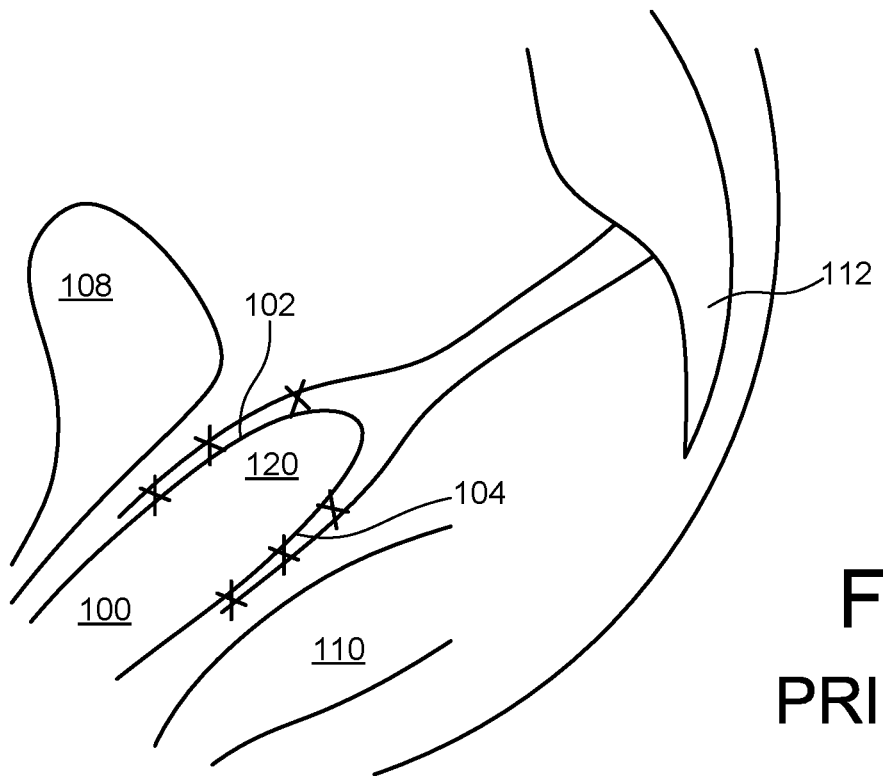
FIG. 1 shows an example of a previous implant and method.
Figure 2:
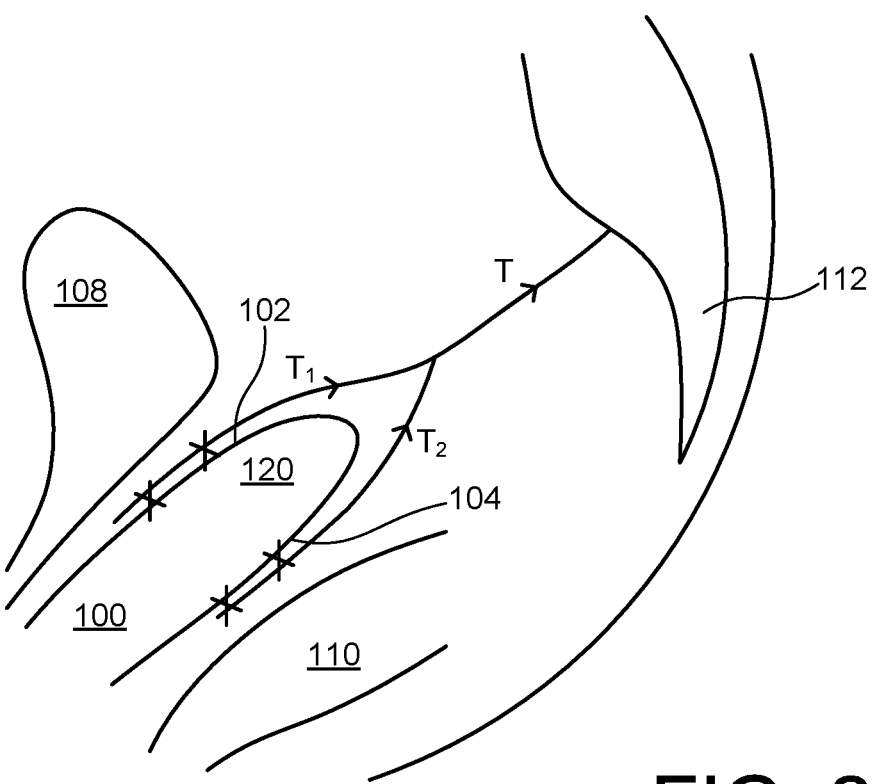
FIG. 2 shows an example of a previous implant and method.

All drawings are schematic and not to scale.

DETAILED DESCRIPTION

Described herein are surgical implants and related methods useful for treating vaginal prolapse in a female patient, e.g., prolapse of non-apical anterior or posterior vaginal tissue such as a cystocele or a rectocele, etc.; or prolapse of apical vaginal tissue, meaning vaginal vault prolapse; or a combination of these. The uterus of the patient will have been removed in a previous or concurrent surgical procedure.

Implants useful in performing any of the described methods include a distal portion to be generally located during use at a region of a sacrum, and a proximal portion to be located during use at a region of vaginal tissue. The distal portion includes a sacral leaf (or "appendage"). The proximal portion includes an anterior vaginal leaf (or "appendage"), and a posterior vaginal leaf (or "appendage"). In use, the anterior vaginal leaf can be placed in contact with and surgically secured to anterior vaginal tissue and can thereby be effective to support the anterior vaginal tissue in a surgical treatment of non-apical anterior vaginal prolapse. The posterior vaginal leaf can be placed in contact with and surgically seemed to posterior vaginal tissue and can thereby be effective to support the posterior vaginal tissue as part of a surgical treatment for non-apical posterior vaginal prolapse. Alternately, or in addition, the combined anterior vaginal leaf and posterior vaginal leaf can be placed at tissue of a vaginal apex or vaginal cuff, to support the vaginal apex in treating apical prolapse. In these treatments, the sacral leaf is suspended by attachment to a posterior location such as at tissue of a region of sacral anatomy, to thereby support the proximal portion of the implant that is attached to the vaginal tissue.

Embodiments of implants useful in a method as described are adjustable to allow for differential placement of tension and support to anterior vaginal tissue relative to posterior vaginal tissue. Exemplary implants include a moveable junction located at the three-way intersection (i.e., junction) of the anterior vaginal leaf, the posterior vaginal leaf, and the sacral leaf. The junction, which can be moved and is not stationary, is the location at which a distal end of the anterior vaginal leaf meets a distal end of the posterior vaginal leaf, and where the distal end of the anterior vaginal leaf and the distal end of the posterior vaginal leaf each meet a proximal end of the sacral leaf. According to the present description, this junction can be moveable along at least a portion of the length of the implant, also moveable relative to a length of the sacral leaf, and also moveable relative to at least one of the two vaginal leafs. Because the junction is moveable, the length of the sacral leaf between the proximal sacral leaf end (which is the same location as the location of the junction) and the distal sacral leaf end, is adjustable, i.e., can be selectively increased or decreased by movement of the junction along the length of the implant. Additionally, because the junction is moveable, the length of at least one of the two vaginal leafs between a proximal vaginal leaf end and a respective distal vaginal leaf end (which is the same location as the location of the junction), is adjustable, i.e., can be increased or decreased by movement of the junction along the length of the implant. According to certain such embodiments of the implant, the length of one of the two vaginal leafs is adjustable by movement of the moveable junction, and the length of the second vaginal leaf is fixed upon movement of the junction. According to other embodiments, the lengths of both of the two vaginal leafs are adjustable, e.g., independently, by movement of the moveable junction relative to each leaf.

An adjustable implant, such as implants described herein that include a moveable junction, can be particularly useful in performing a sacrocolpopexy procedure with desired or improved therapeutic results, e.g., for treating non-apical anterior vaginal prolapse, non-apical posterior vaginal prolapse, or both. The implant, by being adjustable, is capable of being surgically placed in a manner that allows a surgeon to effect differential tensioning and support of the anterior vaginal tissue relative to the posterior vaginal tissue. An adjustable implant, e.g., having a moveable junction, allows the surgeon to position the junction or otherwise adjust lengths of appendages (leafs) relative to the implant, to provide selective support to different supported tissues, which can improve the therapeutic effect of the implant and method of treatment.

Certain useful adjustable implants include a moveable junction, which allows a surgeon to move the location of the tree-way intersection of the two vaginal leafs and the sacral leaf, allowing for the surgeon to adjust a length of one or two of the two vaginal leafs and to optionally provide geometric asymmetry with respect to the lengths of the two vaginal leafs. Allowing for movement of the junction during surgical placement of the implant and optional asymmetry of the lengths of the vaginal leafs can allow for differential tensioning on the anterior and posterior vaginal walls. For example, the moveable junction can be adjusted to increase the relative level of support placed at anterior vaginal issue for treating a patient having anterior vaginal tissue prolapse. Alternately, the moveable junction can be adjusted to increase the relative level of support placed at posterior vaginal issue for treating a patient having posterior vaginal tissue prolapse.

Figure 3:
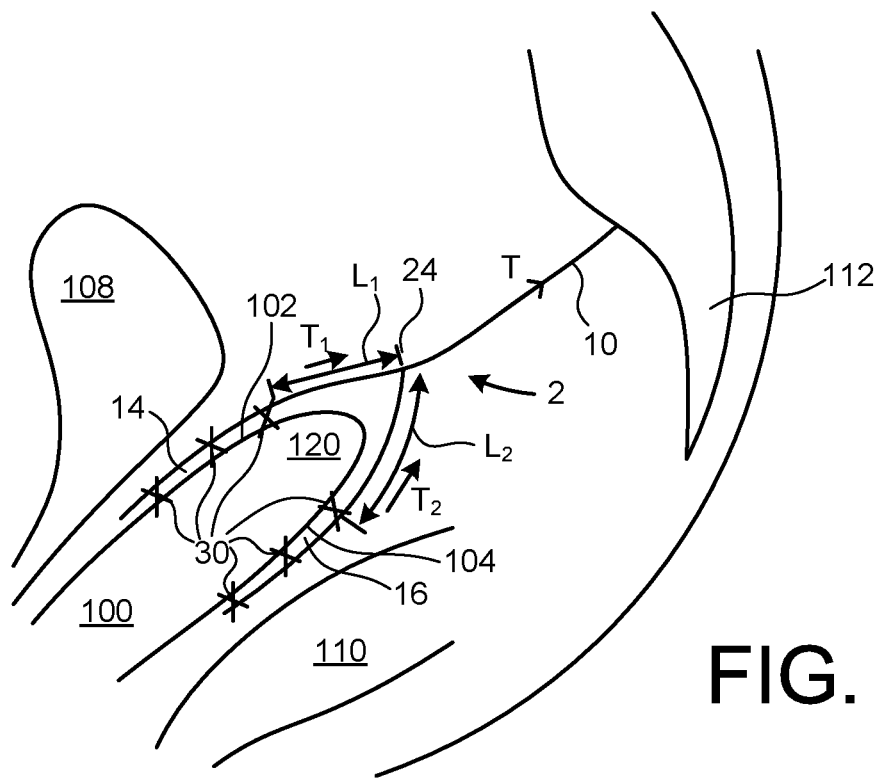
FIGS. 3 and 4 show examples of inventive implants and methods.

FIG. 3 illustrates an example of a Y-shaped implant as described, wherein a moveable junction is positioned along a length of an implant at a location to provide relatively more support to anterior vaginal tissue 102 relative to posterior vaginal tissue 104. As part of implant 2, e.g., as described herein (see below), moveable connector 24 is adjusted and preferably held or locked in place after anterior vaginal leaf 14 and posterior vaginal leaf 16 have been secured to anterior vaginal tissue 102 and posterior vaginal tissue 104, respectively, e.g., by sutures 30. Subsequent to attachment of the vaginal leafs to the respective vaginal tissues, adjustment of moveable connector 24, and locking of moveable connector 24 into place along a length of implant 2, sacral leaf 20 is adjusted and then attached to a region of sacral anatomy such as sacrum 112. The geometric asymmetry (e.g., different lengths) of anterior vaginal leaf 14 and posterior vaginal leaf 16 causes unequal distribution of the tension (T) present in sacral leaf 10, between vaginal anterior leaf 14 and posterior vaginal leaf 16.

Figure 4:
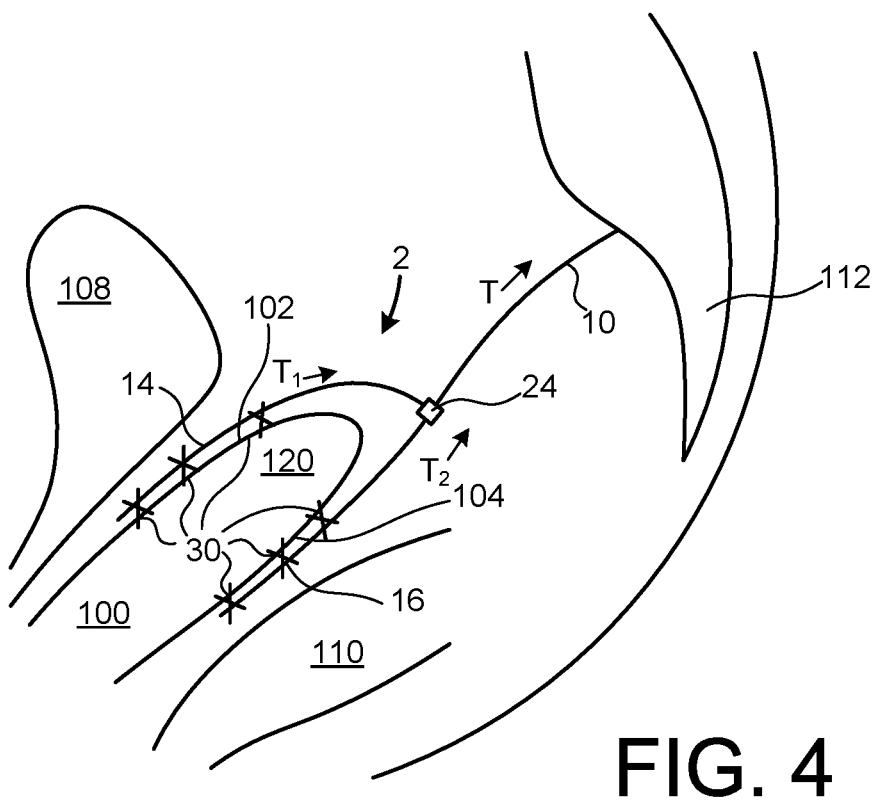

As illustrated at FIG. 4, the total sacral tension T is distributed more to the anterior appendage when compared to the posterior appendage, i.e., tension T1 in anterior vaginal leaf 14 is greater than tension T2 of posterior vaginal leaf 16. Referring to an alternate embodiment, as shown at FIG. 4, the sacral tension T is distributed more to the posterior appendage when compared to the anterior appendage, i.e., tension T2 in posterior vaginal leaf 16 is greater than tension T1 of anterior vaginal leaf 14. According to certain embodiments, and adjustable Y-shaped implant can include a base that has a fixed length of continuous implant material between a distal base end at the distal end of the implant, and a proximal base end at the proximal end of the implant. A sacral leaf extends from a junction, in a distal direction to the distal base end, and is adapted to be attached to tissue at a region of sacral anatomy. A first vaginal leaf, e.g., an anterior vaginal leaf, extends from the junction in a proximal direction to the proximal base end and is adapted to support vaginal tissue, e.g., anterior vaginal tissue. A second direction and is adapted to be attached to vaginal tissue, e.g., posterior vaginal tissue. Each leaf, independently, has a width. The junction is a moveable junction that is moveable along a length of the base between the distal base end and the proximal base end. The first vaginal leaf extends between the proximal base end and the moveable junction. The sacral leaf extends between the moveable junction and the distal base end. The second vaginal leaf, also made of implant material, extends from the moveable junction.

According to these embodiments, each of the two vaginal leafs can be of a single density (material weight) and in the form of a single ply of implant material. The sacral leaf can also be of a single ply and can exhibit the same single density material weight as the vaginal leafs. Alternately, the sacral leaf can be made of two plies (i.e., two layers of implant material) and may be of a double density (double material weight) relative to the vaginal leafs; i.e., a total weight of the sacral leaf material may be twice the weight of a single density vaginal leaf.

The various supportive portions of the implant (the base and the vaginal and sacral leafs) are constructed of surgical implant material adapted to contact tissue in a pelvic region of a patient and to be surgically placed at and secured to the tissue in a manner to support the tissue as a treatment for vaginal prolapse.

The surgical implant material can be a generally planar, flexible, porous implant material adapted to be placed surgically to support vaginal tissue. Many examples of flexible implant materials are known and commercially available, including porous (e.g., mesh) materials that are prepared by assembling strands of fibers such as polymeric monofilaments into a flexible planar woven, non-woven or knit, fabric. Alternate implant materials may be molded, extruded and cut, or otherwise formed to include pores in the form of openings, apertures, or fenestrations adapted to allow tissue ingrowth after implantation.

Suitable implant materials are well known and examples are sold commercially for use as surgical implant materials for supporting anatomical tissue. These include woven, knitted, extruded, or other open pore (porous) materials made from connected strands, fibers, threads, filament (e.g., monofilament), treated film, or the like, which may be natural or synthetic. Exemplary implant materials include woven, non-woven (but still fibrous or filamentary), knitted, or other materials having inter-linked, tied, or otherwise connected filaments or fibers that form multiple fiber junctions and multiple regular or randomly sized and spaced apertures. Implant materials made of monofilament fibers or multi-filament fibers are useful in treating vaginal prolapse, as are materials that include two or more types of different (monofilament, multi-filament, or a combination) fibers assembled together to prepare an implant material. The fiber junctions may be formed by weaving, bonding (e.g., adhesive bonding, thermo-bonding, etc.), tying, ultrasonic welding, knitting, or other junction-forming techniques, including combinations thereof. The size of the resultant openings, pores, apertures, or fenestrations, etc., is sufficient to allow tissue in-growth and fixation of the open pore implant material at contacted tissue after the implant is placed at an anatomical location such as vaginal tissue. As an example, not intended to be limiting, apertures of an open pore implant material may take a form of elliptica4 square, circular, rectangular, or diamond shaped apertures having a diagonal or diameter dimension in a range of about 0.040 inches (1.016 mm) to about 0.055 inches (1.397 mm).

Strands, layers, or filaments, etc., of an open pore implant material can be of any material useful to form a surgical implant. Suitable natural and polymeric materials are biocompatible, optionally bioabsorbable, and may be coated to encourage tissue ingrowth or prevent infection. Examples include nylon, polyethylene terephthalate, polyolefins such as polypropylene and polyethylene, poly-L-lactide (PLLA), polyethylene glycol (PGA), polyester, and any combination of materials. Depending on the desired treatment, the polymer may be absorbable, non-absorbable, or resorbable. Example of commercially available implant materials include those sold under the trade names Prolene™, Deldene™, and Marlex™ implantable materials. Yet another example is woven polypropylene monofilament, knitted with a warp tricot.

Other examples of implant materials include molded materials, e.g., unitary or homogeneous patterned implant materials as described in U.S. Pat. No. 9,060,836, and United States Patent Publication 2014/0257032, the entirety of each of these documents being incorporated herein by reference. Example unitary or homogeneous patterned implants as described in those documents can be constructed of patterned cells formed by way of molding, die casting, laser etching, laser cutting, extruding, or the like. Portions of the implant material (e.g., as formed into an anterior portion) can be formed into sinusoid or other waveform strut members in a manner that allows for desired control of elongation, expansion, contraction along a single or multiple axes of the anterior portion. Stress, tension, and compression distribution can be controlled across specific or localized areas of the implant material or anterior portion. In certain embodiments, a molded implant material can provide for desired uni-dimensional or bi-dimensional elongation properties in a portion of an implant as described, e.g., in an anterior portion. For example, a molded anterior portion may have elongation properties such that the anterior portion will extend (i.e., lengthen) in two dimensions, when pressure is applied to the anterior portion in only a single direction, e.g., the anterior portion may lengthen along to different axes when a force is applied along a single axis.

Figure 5A:
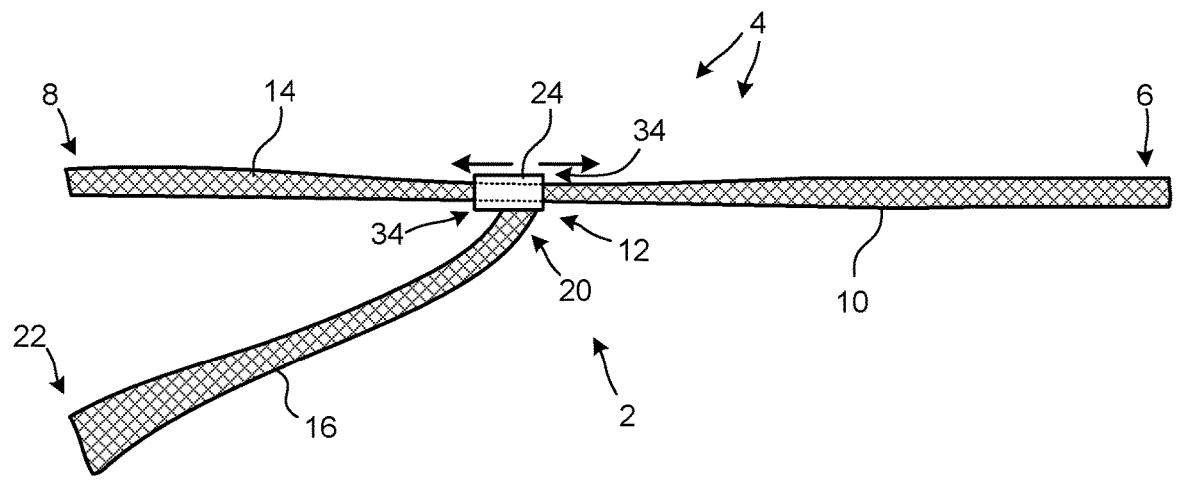
FIGS. 5A, 5B, 6A, 6B, 7A, and 7B show examples of inventive implants.

Referring to now to FIG. 5A (side view) and 5B (top view), implant 2 is a Y-shaped implant that includes a base 4 having a fixed length of implant material between a distal base end 6 at the distal end of the implant, and a proximal base end 8 at the proximal end of the implant. Sacral leaf 10 extends from moveable junction 12 in a distal direction to distal base end 6. First vaginal leaf 14, e.g., an anterior vaginal leaf, extends from junction 12 in a proximal direction to the proximal base end 8. Second vaginal leaf 16, e.g., a posterior vaginal leaf, extends from junction 12 in a proximal direction. Each leaf 10, 14, and 16, independently, has a width.

Junction 12 is a moveable junction that is moveable along a length of base 4 between distal base end 6 and proximal base end 8. First vaginal leaf 14 extends between proximal base end 8 and moveable junction 12, and the length of vaginal leaf 14 can be increased or decreased by movement of connector 12 between proximal base end 8 and distal base end 6 (see arrows at FIGS. 5A and 5B). Sacral leaf 10 extends between the location of moveable junction 12 and distal base end 6.

Figure 5B:
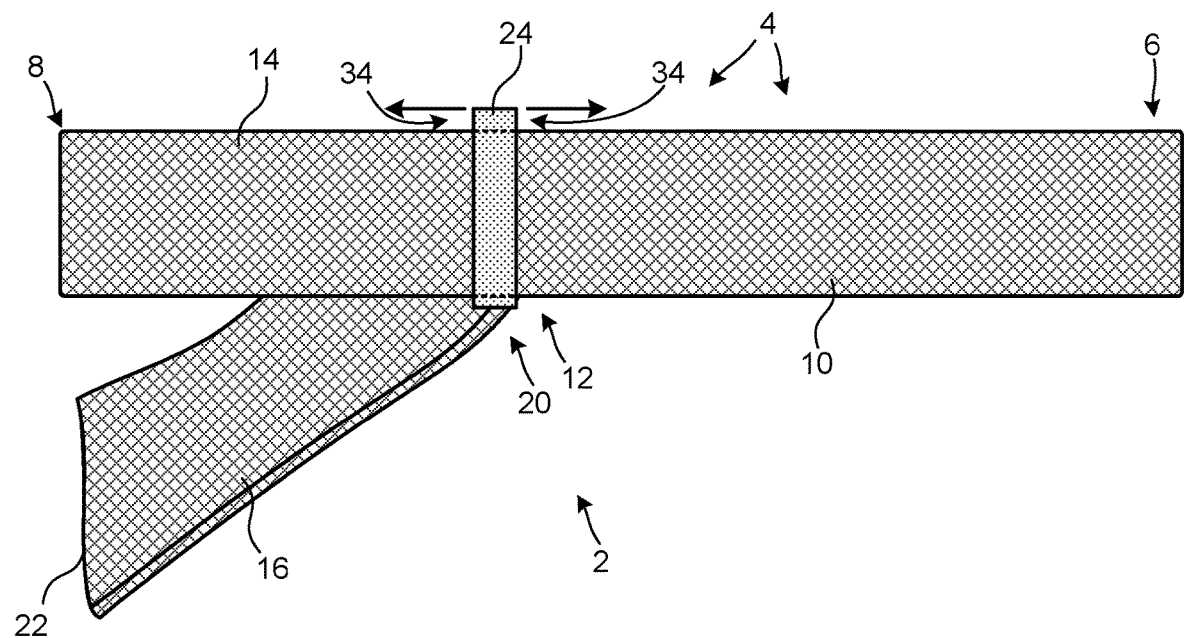

According to implant 2 of FIGS. 5A and 5B, distal end 20 of second vaginal leaf 16 is securely attached to junction 12. The length of second vaginal leaf 16, i.e., the distance between distal end 20 (at the location of its secure attachment to connector 12) and proximal (loose) end 22 is fixed. This fixed length of second vaginal leaf 16 does not change with movement of junction 12 along the length of base 4.

Junction 12, meaning the location of the intersection of leafs 10, 14, and 16, can be moved along the length of base 4. Movement may be made possible, for example, by mechanical connector 24 in the form of a clasp or slider that can freely move along the length of base 4, maintaining an engagement with base 4 and all three of leafs 10, 14, and 16. As illustrated at figures 5A and 5B, connector 24 can include an inner opening 34 (shown in dashed lines) that extends continuously from a distal end to a proximal end of connector 24, while fitting around and containing the width of the implant material (e.g., mesh) that makes up base 4 and allowing for sliding movement of connector 24 over the width and along a length of base 4.

Figure 6A:
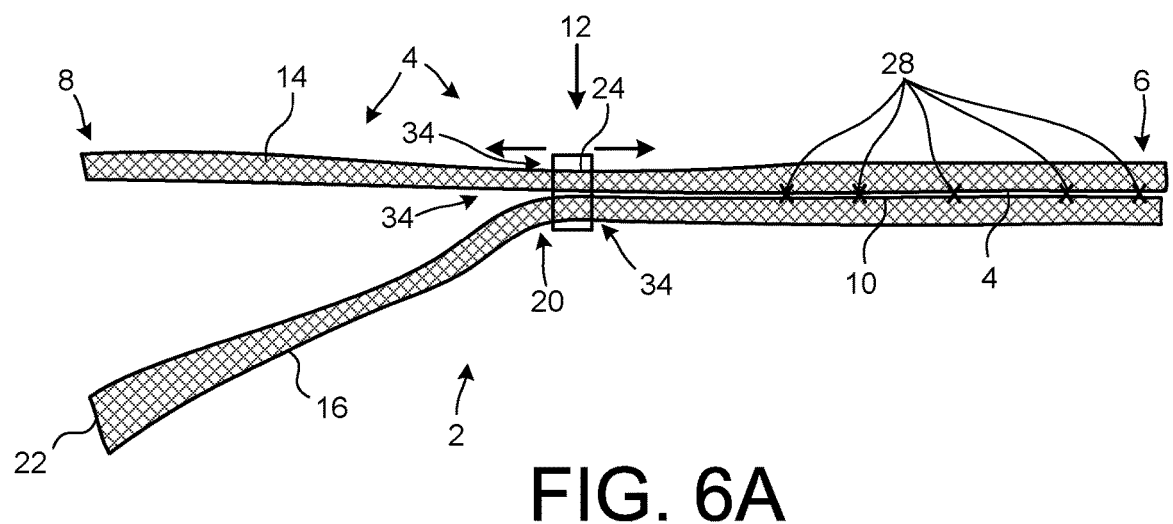

FIG. 6A (side view) and 6B (top view) illustrate an alternate embodiment of implant 2. Illustrated is a Y-shaped implant that includes a base 4 having a fixed length of implant material (e.g., continuous implant material) between a distal base end 6 at the distal end of the implant and a proximal base end 8 at the proximal end of the implant. Sacral leaf 10 extends from moveable junction 12 in a distal direction to distal base end 6. First vaginal leaf 14, e.g., an anterior vaginal teat: extends from junction 12 in a proximal direction to the proximal base end 8. Second vaginal leaf 16, e.g., a posterior vaginal leaf, extends from junction 12 in a proximal direction. Each leaf 10, 14, and 16, independently has a width. A distal portion of base 4 between junction 12 and distal base end 6, this portion of base 4 also being sacral leaf 10, is made of two layers of implant material, i.e., is dual density (double the material weight) relative to vaginal leafs 14 and 16. The two layers are optionally attached at a distal portion of sacral leaf 10, such as by sutures 28 (other attachment means will also be useful).

Figure 6B:
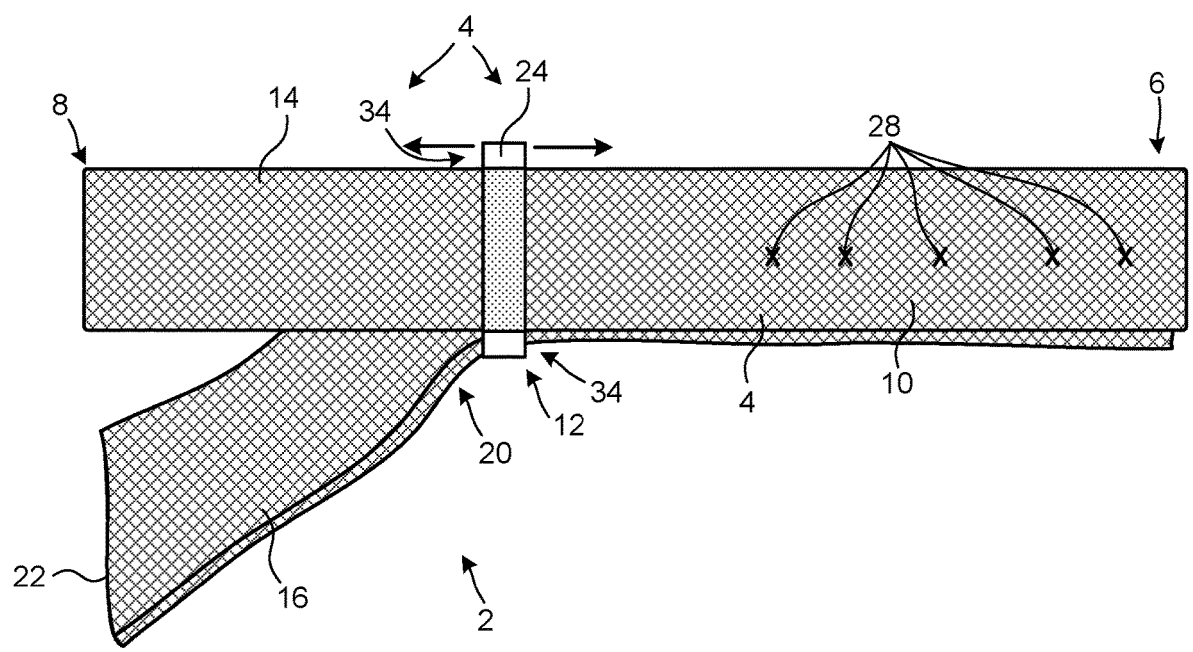

Referring still to FIGS. 6A and 6B, junction 12 is a moveable junction that is moveable along a length of base 4 between distal base end 6, and proximal base end 8. First vaginal leaf 14 extends between proximal base end 8 and moveable junction 12, and the length of vaginal leaf 14 can be increased or decreased by movement of moveable junction 12 between proximal base end 8 and distal base end 6 (see arrows). Sacral leaf 10 extends between the location of moveable junction 12 and distal base end 6. Junction 12, meaning to the location of the intersection of leafs 10, 14, and 16, is moveable, for example by use of mechanical connector 24 in the form of a clasp or slider that can freely move along the length of base 4 while maintaining an engagement with base 4 and all three of leafs 10, 14, and 16. As illustrated at FIGS. 6A and 6B, connector 24 can include an inner opening (shown in dashed lines) that fits around and contains the width of the implant materials (e.g., mesh) that makes up base 4 and allows for sliding movement of connector 24 over the width and along a length of base 4. According to implant 2 of FIGS. 6A and 6B, the location of distal end 20 of second vaginal leaf 16 is controlled by the location of connector 24. The length of second vaginal leaf 16, i.e., the distance between distal end 20 (at the locale of its secure attachment to connector 12) and proximal (loose) end 22 is, therefore, adjustable based on movement of connector 24.

Not shown at FIGS. 5A, 5B, 6A, and 6B, but a preferred feature of a connector 24, is either: a locking engagement that can selectively apply friction between connector 24 and base 4 to cause connector 24 to frictionally engage the implant material of base 4; or, alternately, a frictional engagement (e.g., that is selectively engageable or selectively locking) that can selectively apply and remove friction between connector 24 and base 4 to cause connector 24 to frictionally engage or disengage the implant material of base 4.

Figure 7A:
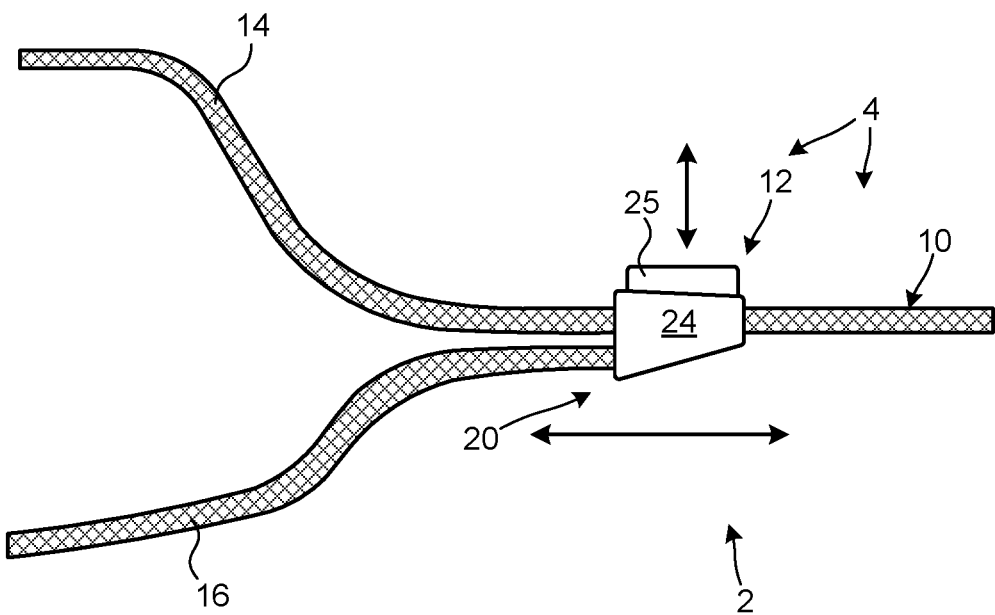
Figure 7B:
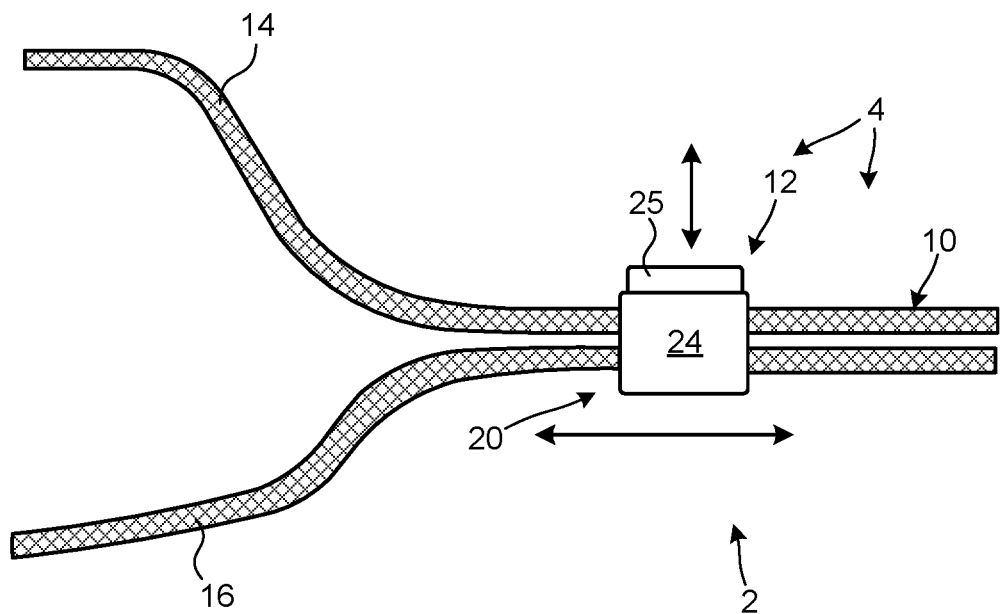

As shown at FIGS. 7A and 7B, implant 2 includes connector 24 having a frictional engagement that can selectively apply and remove friction between connector 24 and base 4. Button 25 can be selectively pressed and released to move up and down (see arrows) relative to base 4, and to cause a frictional engagement of connector 24 (not shown) to frictionally engage or disengage the implant material of base 4. Button 25 is biased to be up (non-depressed) while no pressure is applied to button 25, which causes a frictional engagement of connector 24 to be engaged with base 4, inhibiting and effectively preventing movement of connector 24 along a length of base 4. During use, a surgeon may apply pressure to button 25, which disengages the frictional engagement of connector 24 from base 4 and allows free movement of connector 24 relative to base 4. When the surgeon has identified a desired location of connector 24 along the length of base 4, button 25 is released and the frictional engagement of connector 24 is re-engaged with base 4, again inhibiting and effectively preventing movement of connector 24 along a length of base 4.

Figure 8A:
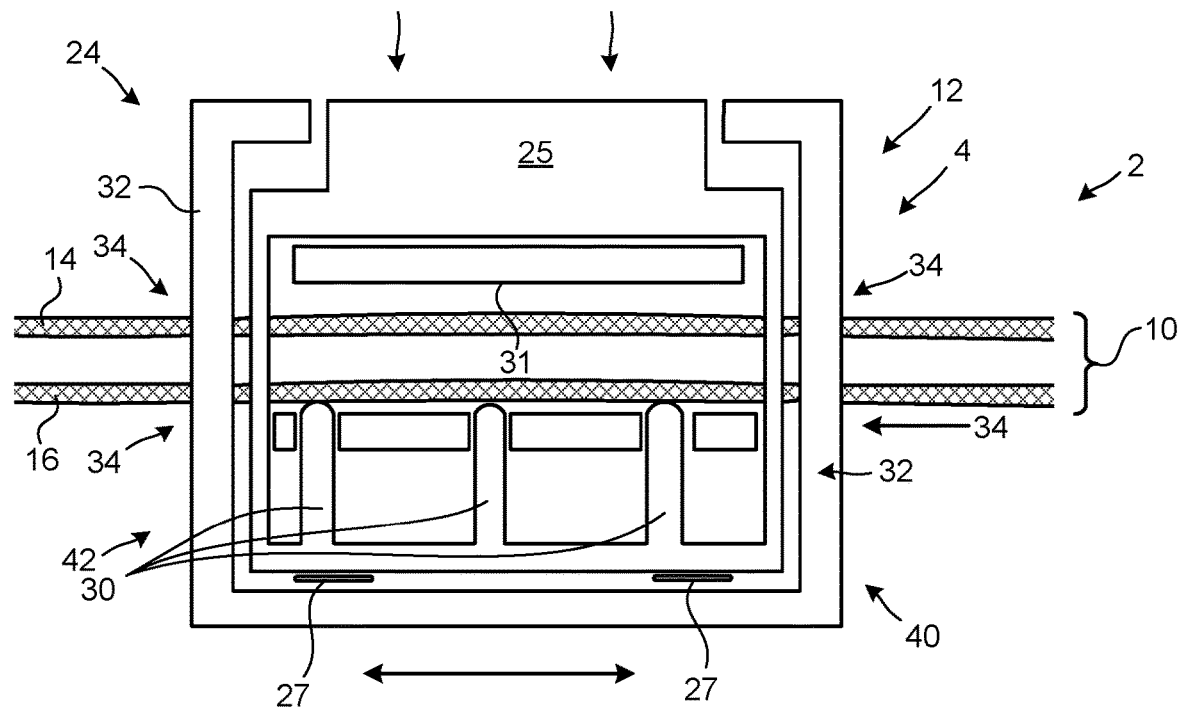
FIGS. 8A, 8B, 9A, and 9B show examples of connector features of inventive implants.
Figure 8B:
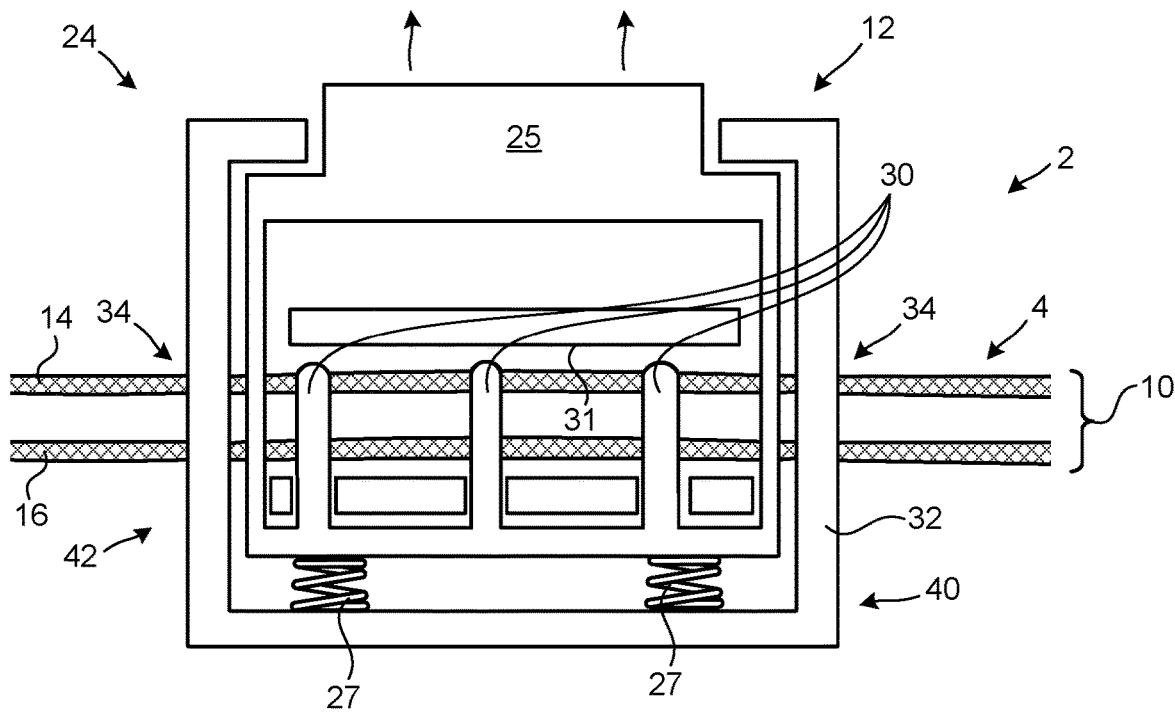

Referring to FIGS. 8A and 8B, illustrated is an example of implant 2, which includes connector 24 at junction 12. Connector 24 includes a frictional engagement that can be selectively engaged with or disengaged from base 4 to prevent or allow, respectively, movement of connector 24 along a length of base 4. Connector 24 includes housing 32, :frictional engagements 30 (which may be teeth, elongate extensions, bumps, points, repeating (e.g., jagged surfaces), or the like), springs 27, and opening 34 extending from distal end 40 of housing 32 to proximal end 42 of housing 32.

Shown at FIG. 8A, button 25 of connector 24 is depressed to compress springs 27, which bias the button to be extended (see FIG. 8B). At FIG. 8A, frictional engagements 30 are depressed (along with button 25) to a position of being frictionally disengaged with the implant material of base 4, also present at the interior of connector 24 and extending within opening 34 between distal end 40 and proximal end 42. In this configuration, with button 25 depressed, connector 24 can be freely moved along a length of base 4 to increase or decrease a length of one or more leafs of implant 2. Frictional engagements 30 as illustrated extend through implant material of base 4, e.g., through holes in the implant material (e.g., pores of an implantable mesh material, or larger openings formed in the implantable mesh material). Alternately, frictional engagements 30 may merely place pressure on the implant material such as by pressing implant material against an opposite surface, 31 (which may be flat or contain its own frictional features), with sufficient force to inhibit or prevent movement of connector 24 along a length of base 4.

Still referring to FIGS. 8A and 8B, button 25 can be pressed and released to move up and down (see arrows) relative to base 4 and to cause frictional engagements 30 internal to connector 24 to frictionally engage or disengage the implant material of base 4. Button 25 is biased by springs 27 to be up while no pressure is applied to button 25, i.e., is biased to cause a frictional engagement of connector 24 with base 4 to thereby inhibit and effectively prevent movement of connector 24 along a length of base 4. During use, a surgeon may apply pressure to button 25, pushing button 25 down to disengage the frictional engagements 30 of connector 24 from base 4 and allow free movement of connector 24 relative to base 4. See FIG. 8A. When the surgeon has identified a desired location of connector 24 along the length of base 4, button 25 is released and frictional engagements 30 of connector 24 re-engaged base 4 to again inhibit and effectively prevent movement of connector 24 along a length of base 4. See FIG. 8B.

Figure 9A:
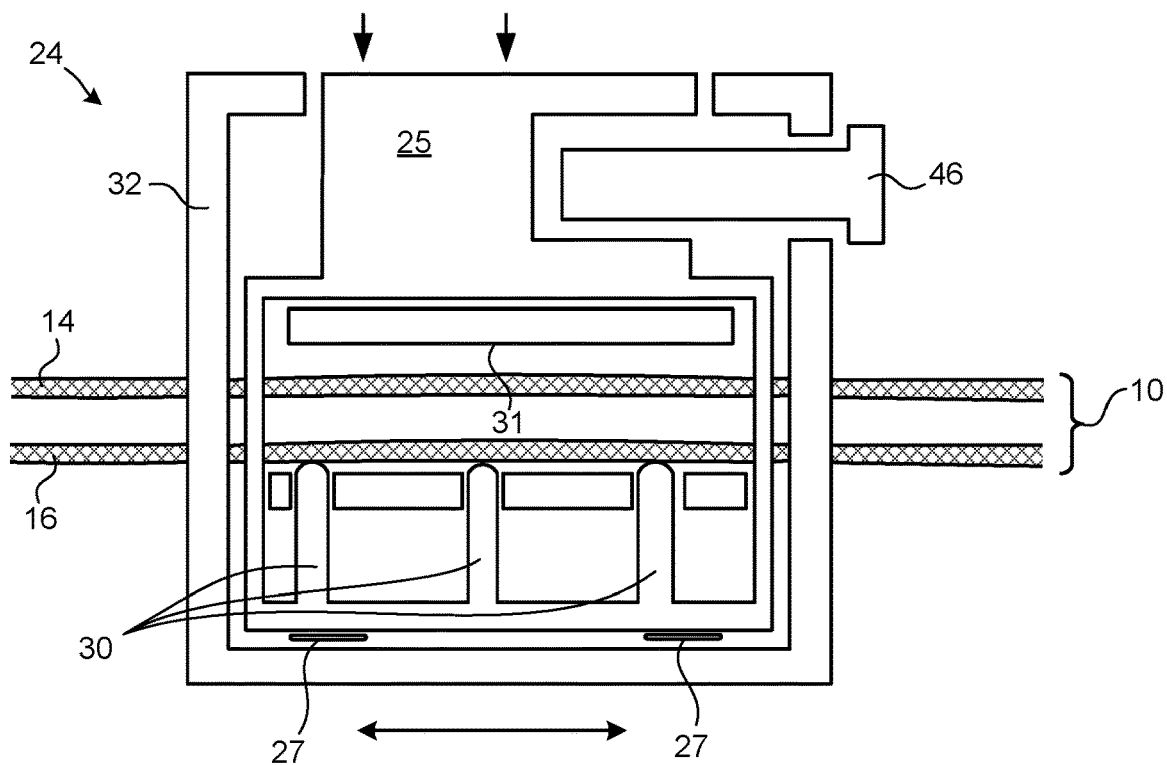
Figure 9B:
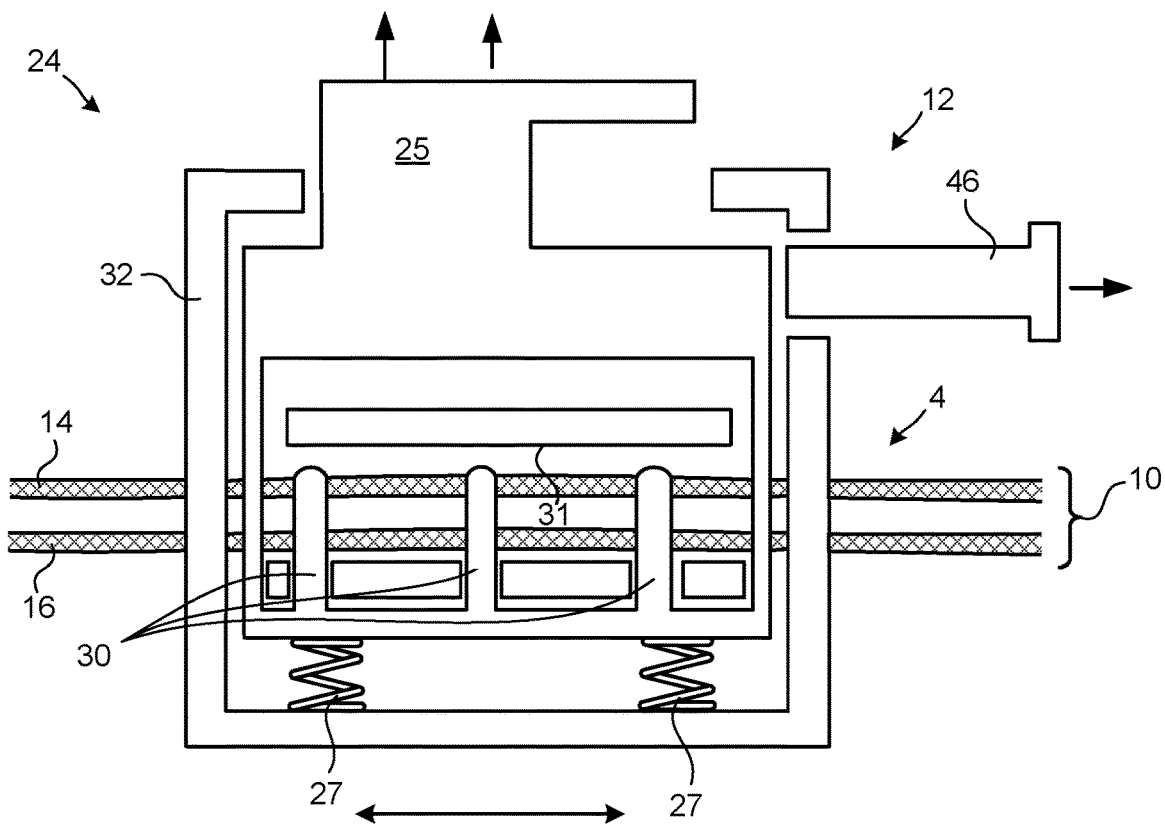

Referring now to FIGS. 9A and 9B, illustrated is another alternate example of implant 2 and connector 24 at junction 12. Connector 24 includes features of the connector of FIGS. 8A and 8A, and additionally includes block 46, which can be selectively engaged (FIG. 9A) and disengaged (FIG. 9B) with button 25. When block 46 is engaged with button 25, button 25 is depressed and frictional engagements 30 are disengaged from the implant material of base 4. In this configuration, connector 24 can be moved relative to base 4. When the surgeon has identified a desired location of connector 24 along the length of base 4, button 25 can be released by disengaging block 46 from button 25, and frictional engagements 30 become engaged with base 4 to inhibit and effectively prevent movement of connector 24 along a length of base 4, as shown at FIG. 9B.

Figure 10A:
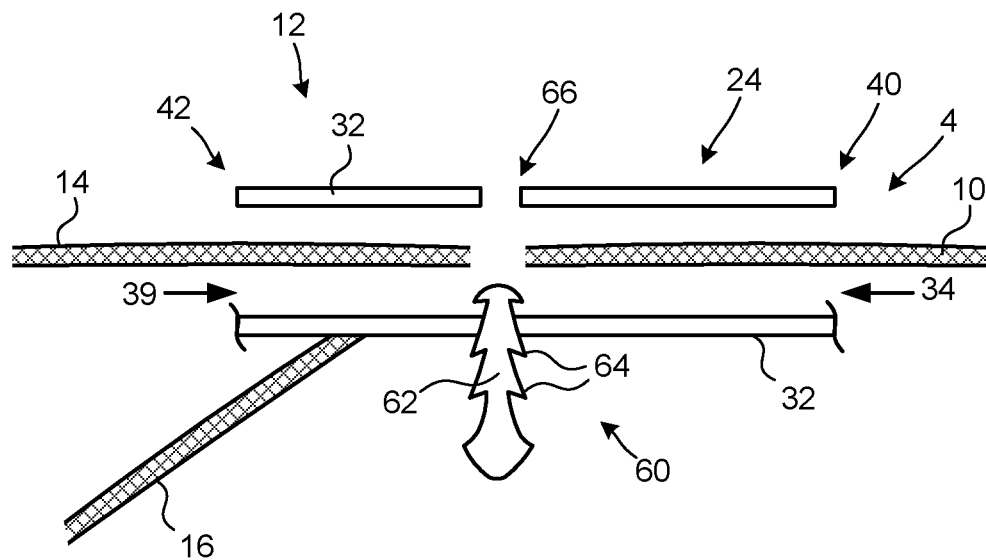
FIGS. 10A and 10B show examples of connector features of an inventive implant.
Figure 10B:
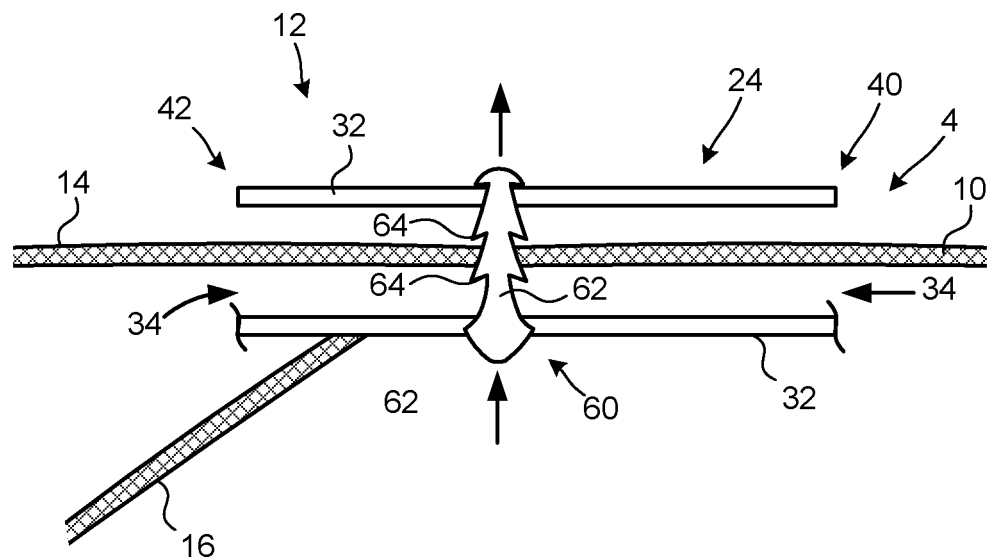

Referring now to FIGS. 10A and 10B, illustrated is an example of implant 2 including alternate connector 24 at junction 12. Connector 24 includes housing 32, moveable frictional engagement 60, opening 34 extending from distal end 40 of housing 32 to proximal end 42 of housing 32, and opening 66 in housing 32 adapted to receive shaft 62, as well as other features similar to connector 24 of FIGS. 8A, SB, 9A, and 9B.

Connector 24 of FIGS. 10A and 10B includes a frictional (e.g., locking) engagement 60 that includes a peg or shaft 62 that includes (optional) extensions or teeth 64 extending therefrom, or another frictional feature that will allow movement of shaft 62 into and through opening 66 and inhibit or prevent reverse movement of engagement 60. Frictional engagement 60 can be initially disengaged to allow movement of connector 24 distally and proximally along a length of base 4. In this configuration, with frictional engagement 60 disengaged, connector 24 can be freely moved along a length of base 4 to increase or decrease a length of one or more leafs of an implant (2). When the surgeon has identified a desired location of connector 24 along the length of base 4, frictional engagement 60 can be pushed toward and into or through the implant material of base 4, then through opening 66 of housing 32. See FIG. 10B, illustrating frictional engagement 60 engaged with base 4 and housing 32 in a manner that inhibits and effectively prevents movement of connector 24 along a length of base 4. The size of shaft 62 may be adapted to engage an opening of an implant material of base 4, such as a pore or other opening or aperture normally in the implant material due to its manufacture by knitting or weaving. Alternately, the implant material of base 4 may have enlarged, cut, or drilled openings and optional reinforcement (e.g., eyelets) through which shaft 62 is adapted to pass. The enlarged. cut, or drilled openings can be located at positions on the base that allow a surgeon to select and then lock connector 24 in place by movement of frictional engagement 60 through the implant material and through opening 66 of housing 32.

Figure 11:
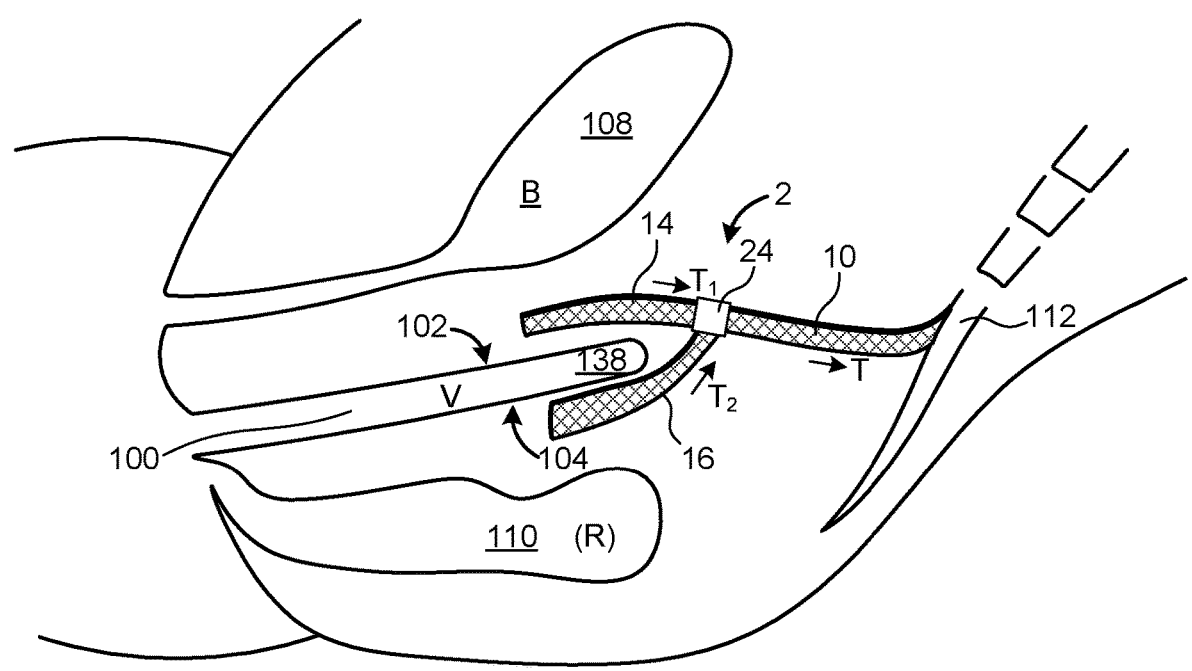
FIGS. 11 and 12 show examples of adjustable implants in a method as described.
Figure 12:
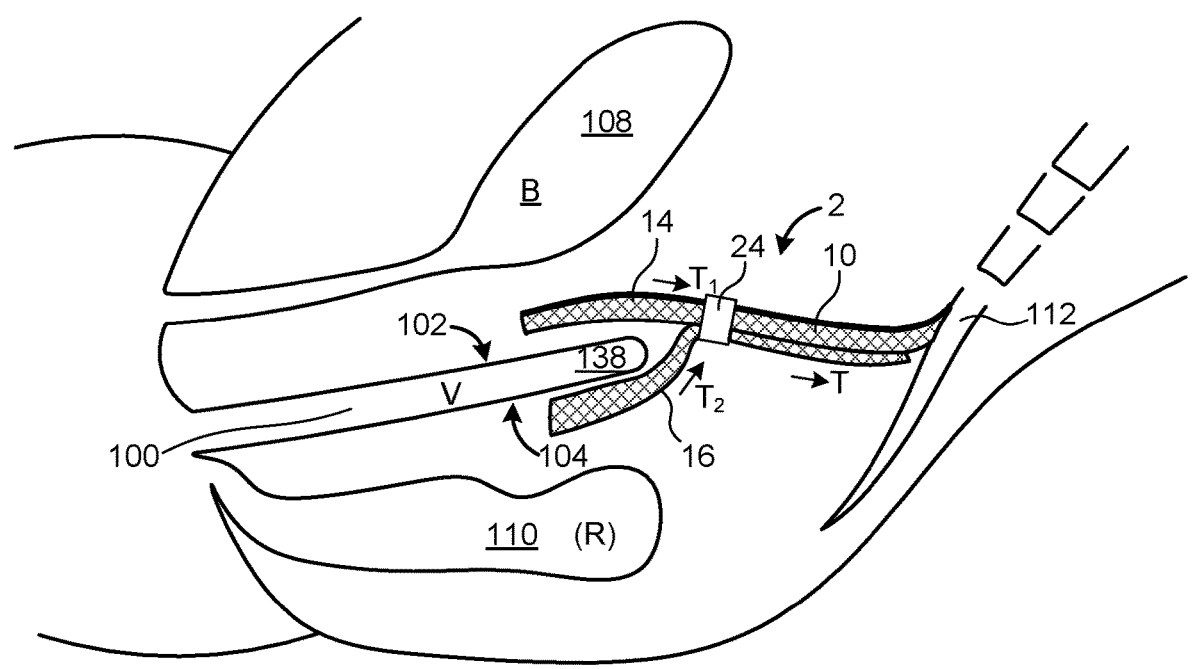

Referring now to FIGS. 11 and 12 (side views), certain relevant features of the female anatomy are illustrated in a patient having her uterus removed. Illustrated anatomy includes vagina (V) 100, anterior vaginal tissue 102, posterior vaginal tissue 104, bladder (B) 108, rectum (R) 110, sacrum (S) 112 (i.e., a region of sacral anatomy that includes the sacral promontory and anterior sacral ligament. etc., none of which being specifically shown), and vaginal vault (i.e., vaginal apex) 120.

A method of placing an implant as described may be performed by surgical techniques that include one or more steps of previously known sacrocolpopexy procedures. The procedure can be useful for treating non-apical vaginal prolapse, apical prolapse, or a combination of non-apical and apical vaginal prolapse. A useful procedure entails suspension (by use of an implant such as a strip of mesh) of non-apical vaginal tissue (e.g., anterior vaginal tissue or posterior vaginal tissue), of a vaginal cuff, or of combinations of these, to a region of sacral anatomy (e.g., the sacrum (bone itself), a nearby sacrospinous ligament, a uterosacral ligament, fascia at or near the sacrum, or an anterior longitudinal ligament at the sacral promontory), via a surgical implant.

The surgical implant can be any surgical implant that will be determined to be useful to perform a method as described herein, that includes placing differential tension or support on tissue of an anterior vagina relative the support placed on tissue of a posterior vagina, in treating non-apical prolapse. Examples of adjustable implants are described and illustrated herein, but the methods of using an adjustable implant as described herein, with differential tensioning of anterior versus posterior tissue, are not limited to and do not require any particular implant design, e.g., do not require use of the presently described adjustable implants. Other adjustable Y-type surgical implants are known, and potentially useful with the methods described herein. See, e.g., United States patent application numbers 2012/0184805 and 2013/0109910, the disclosures of which are incorporated herein by reference, in their entireties. In addition to implants specifically described herein, implants of these patent documents, or adjustment features or adaptations or variations thereof, may be found to be useful in performing a method as described herein, that includes applying differential tension or support to non-apical anterior vaginal tissue relative to non-apical posterior vaginal tissue.

According to example methods, an adjustable Y-shaped implant (e.g., as described) can be placed surgically with a first vaginal leaf being secured to anterior vaginal tissue, a second vaginal leaf being secured to posterior vaginal tissue, and the sacral leaf being secured at tissue in a region of sacral anatomy. After placement of the two vaginal leafs and securement of both leafs to vaginal tissue, a user (e.g., surgeon) can adjust the location of the moveable connector along a length of the base. Movement of the connector along the base can be effective to adjust a length of one or the other of the vaginal leafs (see, e.g., FIGS. 3, 4, and 11), or to adjust lengths of both of the vaginal leafs at the same time (see FIG. 12). When using an implant as shown at FIGS. 5A and 5B, a vaginal leaf of adjustable length may be surgically fixed to vaginal tissue on one side of a vagina (e.g., non-apical anterior vaginal tissue), and a second vaginal leaf of fixed length (relative to junction 12) can be surgically affixed to a second side of the vagina (e.g., non-apical posterior vaginal tissue; see FIGS. 3 and 11). Alternately, a vaginal leaf of adjustable length may be surgically fixed to the posterior vaginal tissue with a vaginal leaf of fixed length being surgically fixed to the anterior vaginal tissue (see FIG. 4).

Example steps of surgical methods include to trim the two vaginal leafs, as desired, to fit anterior and posterior vaginal tissues. The surgeon can then determine the desired level of support and tension to separately apply to each of the anterior and the posterior vaginal tissues depending on the degree and type of the condition, e.g., cystocele, rectocele, or both. The relative amounts of support and tension can be achieved by movement of the moveable connector to adjust the length of one or more of the vaginal leafs; when a desired location of the moveable connector is determined, the connector can be fixed in place, e.g., by actuating a frictional engagement or a locking engagement of the moveable connector. During or after these steps, the surgeon can determine the desired amount of sacral tension to be placed in the sacral leaf and the sacral leaf can be attached to tissue at a region of the patient's sacral anatomy, e.g., the sacral promontory.

Useful methods may be performed through an abdominal incision, through a vaginal incision, or laparoscopically, and optionally by use of robotic surgical equipment. Examples of known methods that are different from those of the present description, but that may have one or more method steps in common, are described in United States Patent Application Publications 2002/0028980; 2010/0184805; 2014/0005471; 2015/0057491; 2013/0109910; and U.S. Pat. Nos. 8,109,867; 8,720,446; and 8,956,276, the entireties of these documents being incorporated herein by reference. Referring to FIG. 11, illustrated is an adjustable Y-implant, e.g., as illustrated at FIGS. 5A and 5B, including anterior vaginal leaf 14, posterior vaginal leaf 16, sacral leaf 10, and an adjustment mechanism (e.g., moveable connector 24). When surgically placed in a patient without a uterus to support non-apical vaginal tissue, implant 2 is placed with anterior vaginal leaf 14 attached to anterior vaginal tissue 102, with posterior vaginal leaf 15 attached to posterior vaginal tissue 102, and with sacral leaf 10 attached to tissue at a region of sacral anatomy, to support implant 2 and the vaginal tissue secured to the vaginal leafs. During implantation, the sliding junction can be positioned by the physician at different locations on the base (4) mesh. The location of the sliding junction along the length of the base (4) will determine how the tension applied to the sacral leaf (T) is distributed between the anterior vaginal leaf (having tension T1) and the posterior vaginal leaf (having tension T2). See FIG. 11, showing T=T1+T2.

FIG. 12 is similar in many respects, but is different in that FIG. 12 shows an implant 2 as illustrated at FIGS. 6A and 6B.

What is claimed is:

1. A Y-shaped surgical implant comprising:
    a base comprising a fixed length of implant material extending between a distal base end and a proximal base end, the base defining a sacral leaf, a first vaginal leaf, and a width,
    a moveable junction that is moveable along the length between the distal base end and the proximal base end, wherein
    the first vaginal leaf extends between the proximal base end and the moveable junction,
    the sacral leaf extends between the moveable junction and the distal base end, and
    a second vaginal leaf comprising implant material extends from the moveable junction, the second vaginal leaf has a second vaginal leaf length between a distal second vaginal leaf end at the moveable junction, and a loose proximal vaginal leaf end, and the second vaginal leaf length is adjustable by movement of the moveable junction along the length of the base.

2. An implant of claim 1 wherein the moveable junction is moveably attached to the base along a width of the base in a manner that allows the moveable junction to maintain engagement with the base while being moved along the length of the base.

3. An implant of claim 1 wherein the first vaginal leaf has a length between the first base end and the location of the moveable junction along the length of the base, and the length of the first vaginal leaf is adjustable by movement of the moveable junction along the length of the base.

4. An implant of claim 1 wherein the sacral leaf has a length between the base end and the location of the moveable junction along the length of the base, and the length of the sacral leaf is adjustable by movement of the movable junction along the length of the base.

5. An implant of claim 1 wherein the moveable junction includes a slider securely attached to the distal end of the second vaginal leaf the slider being moveably attached to the base along a width of the base in a manner that allows the slider to maintain engagement with the base while moving along the length of the base.

6. An implant of claim 1 wherein the moveable junction includes a frictional engagement that can be selectively placed in an open configuration or a closed configuration, wherein with the frictional engagement in the open configuration the moveable junction can be moved along the length of the base while maintaining engagement with the base, and with the frictional engagement in the closed configuration the frictional engagement frictionally prevents movement of moveable connection along the length of the base.

7. An implant of claim 6 wherein the moveable junction is selected from a spring-loaded frictional engagement that is biased open, and a spring-loaded frictional engagement that is biased closed.

8. An implant of claim 1 adapted to allow the first vaginal leaf and the second vaginal leaf to be secured to non-apical anterior and posterior vaginal tissue, while the sacral leaf extends to and is secured to tissue at a region of a sacrum.

9. A method of treating vaginal vault prolapse in a female patient, the method comprising:
    providing a Y-shaped implant comprising an anterior vaginal leaf, a posterior vaginal leaf, and a sacral leaf, the three leafs being connected at a junction, the junction includes a frictional engagement that can be selectively placed in an open configuration or a closed configuration, at least one of the anterior vaginal leaf and the posterior vaginal leaf being an adjustable-length vaginal leaf wherein a length of the at least one anterior vaginal leaf and posterior vaginal leaf between the junction and a proximal end of the vaginal leaf is adjustable,
    attaching the anterior vaginal leaf to anterior vaginal tissue of the patient,
    attaching the posterior vaginal leaf to posterior vaginal tissue of the patient, and
    adjusting the length of the at least one adjustable-length vaginal leaf to increase or to decrease the amount of tension applied by the implant to the anterior vaginal tissue, relative to the amount of tension applied by the implant to the posterior vaginal tissue.

10. A method of claim 9 further comprising, after attaching the anterior vaginal leaf to the anterior vaginal tissue and after attaching the posterior vaginal leaf to the posterior vaginal tissue, adjusting the length of the at least one adjustable-length vaginal leaf to increase or to decrease the amount of tension applied by the implant to the anterior vaginal tissue, relative to the amount of tension applied by the implant to the posterior vaginal tissue.

11. A method of claim 9 further comprising, after adjusting the length, attaching the sacral leaf to tissue at a region of sacral anatomy of the patient.

12. A method of claim 9 wherein
the method includes treating cystocele, and
the adjusting step includes placing a greater amount of tension on the non-apical anterior vaginal tissue compared to the amount of tension placed on the posterior vaginal tissue.

13. A method of claim 9 wherein
the method includes treating rectocele, and
the adjusting step includes placing a greater amount of tension on the non-apical posterior vaginal tissue compared to the amount of tension placed on the posterior vaginal tissue.

14. A method of claim 9 wherein the adjusting step includes adjusting the length of the at least one adjustable-length vaginal leaf such that a length of implant material between the junction and a first location of attachment of the anterior vaginal leaf to the anterior vaginal tissue is less than a length of implant material between the junction and a first location of attachment of the posterior vaginal leaf to the posterior vaginal tissue.

15. A method of claim 9 wherein the adjusting step includes adjusting the length of the at least one adjustable-length vaginal leaf such that a length of implant material between the junction and a first location of attachment of the anterior vaginal leaf to the anterior vaginal tissue is greater than a length of implant material between the junction and a first location of attachment of the posterior vaginal leaf to the posterior vaginal tissue.

16. A method of claim 9 wherein
the method includes treating rectocele, enterocele, or a combination thereof, and
the adjusting step includes placing a greater amount of tension on the posterior vaginal tissue compared to the amount of tension placed on the anterior vaginal tissue.

17. A method of claim 9 wherein the implant comprises
a base comprising a length of open pore implant material between a first end and a second end, the sacral leaf at the first end and the anterior vaginal leaf at the second end, and a width, and
the posterior vaginal leaf comprising a loose end, a proximal end, a length between the loose end and the proximal end, and a width,
wherein the second vaginal leaf meets the base to form the moveable junction that allows movement of a location of the junction along the length of the base.

18. A Y-shaped surgical implant comprising:
a base comprising a fixed length of implant material extending between a distal base end and a proximal base end, the base defining a sacral leaf, a first vaginal leaf, and a width,
a moveable junction that is moveable along the length between the distal base end and the proximal base end, the moveable junction includes a frictional engagement that can be selectively placed in an open configuration or a closed configuration,
wherein
the first vaginal leaf extends between the proximal base end and the moveable junction,
the sacral leaf extends between the moveable junction and the distal base end, and
a second vaginal leaf comprising implant material extends from the moveable junction.

19. The implant of claim 18, wherein when the frictional engagement is in the open configuration the moveable junction can be moved along the length of the base while maintaining engagement with the base, and when the frictional engagement is in the closed configuration the frictional engagement frictionally prevents movement of the moveable junction along the length of the base.

20. An implant of claim 18, wherein the frictional engagement is selected from a spring-loaded frictional engagement that is biased open, and a spring-loaded frictional engagement that is biased closed.

\* \* \* \* \*